United States Patent [19]

Nakaoku et al.

[11] Patent Number: 4,826,840

[45] Date of Patent: * May 2, 1989

[54] CEREBRAL PROTECTING AGENT

[75] Inventors: Shozo Nakaoku; Eiji Imai, both of Takayama; Yasuhiro Oshika, Sagamihara; Kazuo Ohira, Takayama, all of Japan

[73] Assignee: Taiyo Pharmaceutical Industry Co., Ltd., Takayama, Japan

[*] Notice: The portion of the term of this patent subsequent to Aug. 9, 2005 has been disclaimed.

[21] Appl. No.: 64,017

[22] Filed: Jun. 19, 1987

[30] Foreign Application Priority Data

Mar. 27, 1987 [JP] Japan .................................. 62-73145

[51] Int. Cl.⁴ ........................................... C07D 405/04
[52] U.S. Cl. .................... 514/218; 540/575; 544/378; 514/254
[58] Field of Search .......... 544/377, 375, 378; 540/575; 514/218, 254

[56] References Cited

U.S. PATENT DOCUMENTS 4,393,226 7/1983 Witiak et al. ................ 549/433
4,443,448 4/1984 Bogeso ................ 514/255

OTHER PUBLICATIONS

Journal of Medicinal Chemistry, 21, No. 12, pp. 1313-1315, 1978.

Primary Examiner—Robert Gerstl
Assistant Examiner—Miriam Sohn
Attorney, Agent, or Firm—Oblon, Fisher, Spivak, McClelland & Maier

[57] ABSTRACT

An indene compound of the general formula (I):

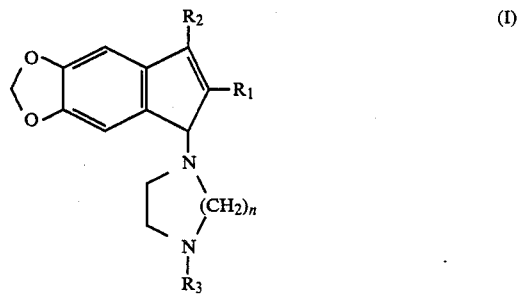

in which $R_1$ represents a lower alkyl group, $R_2$ represents a hydrogen atom, an aryl group or lower alkyl group, $R_3$ represents an alkyl group, and n indicates an integer of 2 or 3; or a salt thereof. The compound has very strong ameliorating or improving effects on cerebral circulation and metabolism, and thus is very useful for ameliorating, or suppressing the progress of, disturbances of brain tissues and functions.

2 Claims, No Drawings

CEREBRAL PROTECTING AGENT

BACKGROUND OF THE INVENTION (1) Field of the Invention

This invention relates to an ameliorant of cerebral circulation and metabolism, and more particularly, to an ameliorant of cerebral circulation and metabolism comprising as an effective component thereof an indene compound of the general formula (I):

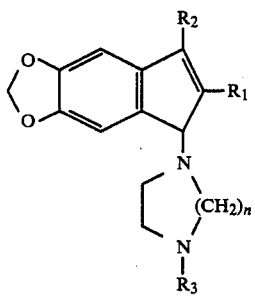

(I)

in which $R_1$ represents a lower alkyl group, $R_2$ represents a hydrogen atom, an aryl group or lower alkyl group, $R_3$ represents an alkyl group, and n indicates an integer of 2 or 3; or a salt thereof.

(2) Description of the Prior Art

Ameliorants of cerebral circulation and metabolism can be defined as the medicines for ameliorating self symptoms and neurologic or metal symptoms due to disturbances of cerebral vessel, and for improving and suppressing the progress of disorders of brain tissues and functions caused by hypoxia. They are also called the brain protective agents.

Practically, these medicines are used for ameliorating or improving such cerebral diseases or disorders as cerebral hemorrhage, cerebral thrombosis, cerebral embolism, subarachnoidal hemorrhage, transient ceretral ischemic attack, hypertensive encephalopathy, cerebral vessel disturbances, brain edema, injuries on the head, the so-called brain apoplexy, Alzheimer disease, etc.

Hitherto, flunarizine, nicardipine, vinpocetine and the likes are known in the art as medicines for curing postsymptoms of cerebral disorders such as cerebral hemorrhage. These compounds, however, do not possess sufficient efficacies as ameliorants of cerebral circulation and metabolism.

SUMMARY OF THE INVENTION

The present inventors have synthesized various compounds and examined their medicinal actions, and found that novel compounds as represented by the above formula (I) had an excellent ameliorating action on the cerebral circulation and metabolism. Such findings have lead to the completion of this invention.

Accordingly, an object of this invention is to provide an ameliorant of cerebral circulation and metabolism comprising as an effective component thereof the compound represented by the above formula (I).

DETAILED DESCRIPTION OF THE INVENTION AND PREFERRED EMBODIMENTS

The compound of the formula (I) may be prepared, for example, by reacting an indene derivative (III) with a secondary amine (II) according to the following reaction scheme:

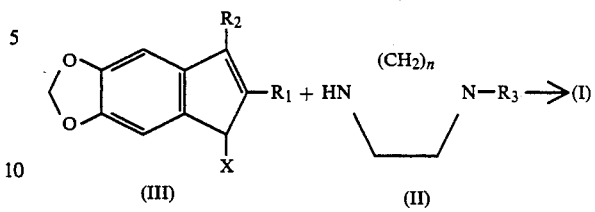

in which X represents a halogen atom, $R_1$, $R_2$, $R_3$ and n have the same meanings as defined above.

The reaction can be carried out by stirring the mixture of the above compounds in an organic solvent such as dimethylsulfoxide at room temperature or under ice cooling.

The raw material represented by the formula (III), is a novel compound discovered by the present inventors and may be prepared, for instance, according to the following reaction scheme:

$$\text{Piperonal} + R_2\text{—CO—CH}_2\text{—}R_1 \xrightarrow{\text{HBr gas or HCl gas}} \text{(III)}$$

in which $R_1$ and $R_2$ have the same meanings as defined above.

More specifically, the compound (III) can be prepared according to the method as described n detail hereinafter in Referential Examples.

As other compounds represented by the formula (II), 1-alkylpiperazine such as 1-methylpiperazine, 1-propylpiperazine and 1-butylpiperazine, and 1-alkylhomopiperazine such as 1-propylhomopiperazine are preferably employed.

The indene compound (I) thus prepared may be converted, as required, into an inorganic salt such as hydrochloride and hydrobromide, or an organic salt such as maleate or fumarate by conventional methods.

Beside the above salts, any isomers of the indene compounds as represented by the formula (I) can be used for the purpose of this invention.

The ameliorants of cerebral circulation and metabolism containing the compound of the formula (I) may be made into forms either for oral administration such as tablets, capsules, powder, granules, and syrups, or forms for intravenous administration. Various ingredients other than the compound (I) may be incorporated in the dosage for oral administration. These include diluents such as lactose, corn starch and crystalline cellulose; lubricants such as magnesium stearate; binders such as hydroxypropyl cellulose; coloring agents; flavoring agents; sweetening agents; and the like.

A dose of the ameliorant of cerebral circulation and metabolism of this invention to be administered may be usually from 1 to 500 mg, and more practically from 5 to 200 mg, as indene compounds per day for adult, although the quantity may vary depending on the age, body weight and symptoms of the patients.

Since the compounds of the formula (I) has very strong ameliorating or improving effects on cerebral circulation and metabolism as compared with flunarizine, nicardipine and the like which are the conventionally used compounds, the inventive compound is very useful for ameliorating, or suppressing the progress of, disturbances of brain tissues and functions.

The present invention will hereinafter be described further by the following Referential Examples and Examples. It should, however, be understood that the invention shall not be limited in any manner whatsoever by these examples.

Referential Example 1
1-bromo-2-n-butyl-5,6-methylenedioxyindene

Hydrogen bromide gas was bubbled into a solution of 500 mg of piperonal and 400 mg of n-capronaldehyde in 5 ml of methanol for one and one half hours. The reaction mixture was colored first in red and then into green. The mixture was poured into ice water, extracted with ether, washed with a diluted aqueous sodium bicarbonate and with water, and then dried over anhydrous magnesium sulfate. The solvent was evaporated off in vacuo and the residue was purified by column chromatography on silica gel (eluent: a 10:1 mixture of n-hexane and ether) to give 750 mg of light yellow crystals at a yield of 77%. The substance had a melting point of 63°–64° C.

Referential Example 2
1-chloro-2-n-butyl-3-methyl-5,6-methylenedioxyindene The procedures of Referential Example 1 were exactly followed, except that 2-heptanone and hydrogen chloride gas were used instead of capronaldehyde and hydrogen bromide gas, respectively, thus affording a light yellow oily substance at a yield of 50%.

IR$\nu_{max}^{neat}$ cm$^{-1}$: 2925, 1460, 1330, 1270, 1160, 1030, 930, 860

Referential Example 3
1-bromo-2-n-butyl-3-phenyl-5,6-methylenedioxyindene The procedures of Referential Example 1 were followed, except that n-hexanophenone was used instead of capronaldehyde, to give a light yellow oily substance at a yield of 57%.

IR$\nu_{max}^{neat}$ cm$^{-1}$: 2920, 1460, 1360, 1280, 1145, 1030, 940, 700

Example 1

(i) 1-(4-methylpiperazinyl)-2-n-butyl-5,6-methylenedioxyindene (compound 1a)

12 g of 1-bromo-2-n-butyl-5,6-methylenedioxyindene was added to a stirred solution of 8.2 g of 1-methylpiperazine and 4.3 g of sodium carbonate in 250 ml of dimethylsulfoxide at room temperature. The mixture was stirred for 1 hour at room temperature, poured into ice water, and then extracted with ethyl acetate. The extract was washed with water, dried over anhydrous magnesium sulfate, and then concentrated in vacuo. The residue was purified by column chromatography on silica gel (eluent: a 30:1 mixture of chloroform and methanol) to give 12 g of colorless crystals (compound 1a) at a yield of 93.8%.

Melting point: 83°–85° C.
IR$\nu_{max}^{KBr}$ cm$^{-1}$: 2925, 1470, 1320, 1145, 1035, 865

(ii) Monohydrochloride of 1-(4-methylpiperazinyl)-2-n-butyl-5,6-methylenedioxyindene (compound 1b)

4.9 g of the compound 1a was dissolved in 50 ml of methanol, to which added was 20 ml of methanol containing 1.33 ml of 36% hydrogen chloride. The mixture was concentrated under reduced pressure. The residue was recrystallized from 50 ml of water, affording 3.7 g of monohydrochloride of the compound 1a (compound 1b) at a yield of 69%.

Melting point: 210°–213° C. (decomposed)
IR$\nu_{max}^{KBr}$ cm$^{-1}$: 3500, 2950, 2800–2200, 1470, 1295, 1035, 865

(iii) Dihydrochloride of 1-(4-methylpiperazinyl)-2-n-butyl-5,6-methylenedioxyindene (compound 1c)

12 g of the compound 1a was dissolved in 50 ml of chloroform and 20 ml of ethanol, into which an excess amount of hydrogen chloride gas was bubbled under ice cooling. The mixture was concentrated under reduced pressure, and the residue was thoroughly washed with ether. The residue was recrystallized from 450 ml of isopropylalcohol and 130 ml of ether, to give 9.7 g of dihydrochloride of the compound 1a (compound 1c) at a yield of 68%.

Melting point: 197°–198° C. (decomposed
IR$\nu_{max}^{KBr}$ cm$^{-1}$: 3450, 1950, 2800–2000, 1475, 1335, 1037

Examples 2–6

The compounds listed in Table 1 were prepared according to the same manner as described in Example 1, using, instead of 1-methylpiperazine, secondary amines which are the known compounds, and the compounds used in Referential Examples 1 to 3.

TABLE 1

| Examples | Compounds | In the formula (I) R1 | R2 | R3 | n | Characteristics | Salt | Yield (%) | m. p. (°C.) | IR$\nu_{max}^{neat\ or\ KBr}$ (cm$^{-1}$) |
|---|---|---|---|---|---|---|---|---|---|---|
| 2(i) | 2a | n-C$_4$H$_9$ | H | —CH$_2$—CH$_2$—CH$_3$ | 2 | Oily Substance | | 95 | | 2925, 1460, 1320, 1150, 1035, 935, 850, 750 |
| 2(ii) | 2b | " | H | " | 2 | Crystals | Monohydrochloride | 68 | 213–215 (decomposed) | 2950, 2925, 2750–2000, 1470, 1315, 1120, 1040, 980 |
| 2(iii) | 2c | " | H | " | 2 | Crystals | Dihydrochloride | 93 | 196–197 (decomposed) | 2950, 2925, 2780–2000, 1470, 1325, 1030 |
| 3(i) | 3a | " | H | —(CH$_2$)$_3$—CH$_3$ | 2 | Oily Substance | | 91 | | 2925, 1460, 1320, 1150, 1035, 860 |
| 3(ii) | 3b | " | H | " | 2 | Crystals | Dihydrochloride | 72 | 177–180 (decomposed) | 2920, 2700–2100, 1470, 1320, 10 920 |
| 4(i) | 4a | " | H | —CH$_2$—CH$_2$—CH$_3$ | 3 | Oily Substance | | 62 | | 2925, 1460, 1315, 1035, 940, 860 |
| 4(ii) | 4b | " | H | " | 3 | Crystals | Dihydrochloride | 74 | 140–144 | 2925, 2750–2100, 1470, 1320, 1030, 930 |
| 5(i) | 5a | " | —CH$_3$ | " | 2 | Oily | | 65 | | 2925, 1460, 1330, |

TABLE 1-continued

| Examples | Compounds | In the formula (I) R1 | R2 | R3 | n | Character- istics | Salt | Yield (%) | m. p. (°C.) | IR$\nu_{max}^{neat\ or\ KBr}$ (cm$^{-1}$) |
|---|---|---|---|---|---|---|---|---|---|---|
| | | | | | | Substance | | | | 1270, 1150, 1040, 935, 760 |
| 5(ii) | 5b | " | " | " | 2 | Crystals | Dihydro- chloride | 71 | 195–197 | 2925, 2750–2000, 1470, 1330, 1270, 1030, 930 |
| 6(i) | 6a | " | —C$_6$H$_5$ | " | 2 | Oily Substance | | 58 | | 2920, 1455, 1270, 1140, 1030, 935, 750 |
| 6(ii) | 6b | " | " | " | 2 | Crystals | Dihydro- chloride | 70 | 138–143 | 2920, 2750–0, 1590, 1450, 1, 1030, 930, 700 |

EXAMPLE 7

Protective Effect against KCN Death ddY male mice (age: 6 weeks, weight: 18–21 g) were used for the experiment after they are preliminary bred in the metal cage for 1 week in in a breeding room in which the temperature was controlled at 22±2° C. and the humidity was at 55±10%. They were given pelleted diet (CE-2, product of Nippon Crea) and water ad lib. Prior to submitting the animals to the experiment, they were fasted for 21–23 hours.

The test compounds were dissolved or suspended in 0.3% methylcellulose solution and were adjusted to be administered in the quantity of 0.1 ml/10 g B.W. Each test compound at 40 mg/kg was orally administered. Two (2) hours thereafter a lethal dose of KCN (2.1 mg/kg) was given intravenously through caudal vein over the period of 15 seconds and the survival rate was determined.

The Statistical analysis of the difference between the tested group and the control was performed using $x^2$-test. The results are shown in Table 2. The test compounds at 40 mg/kg p.o. showed significant protective effect against the death induced by KCN. Thus, these compounds have been recognized as possessing the brain protective action.

TABLE 2

| Test Compounds | Survived Animals/ Tested Animals | Rate of Survival (%) |
|---|---|---|
| 1c | 7/9 | 78*** |
| 2b | 5/10 | 50*** |
| 3b | 3/9 | 33** |
| 4b | 5/9 | 56*** |
| 5b | 5/9 | 56*** |
| 6b | 3/10 | 30* |
| Controls | 0/19 | 0 |

*P < 0.05, P < 0.01, *P < 0.001

Example 8

Effect on Brain Ischemia Model by MgCl$_2$ ddY male mice (age: 7 weeks) having been preliminary bred in the same manner as in Example 7 were fasted and orally administered with the test compounds dissolved in 0.3%methylcellulose solution. Two (2) hours later, 0.05 ml of saturated solution of MgCl$_2$ was intravenously administered rapidly through the caudal vein. The survival rate was determined as the period of time until final gasping.

As shown in Table 3, the compound 1c and 2b at the doses of about 40 mg/kg demonstrated the significant prolongation of survival time dose-dependency, and thus were recognized as having the brain protective action.

TABLE 3

| Test Compounds | Quantity Administered (mg/kg oral) | Numbers of Animals | Survival Time (sec.) |
|---|---|---|---|
| 1c | 40 | 8 | 28.8 ± 0.6*** |
| | 80 | 9 | 32.3 ± 0.6*** |
| 2b | 40 | 10 | 28.3 ± 1.5* |
| | 80 | 8 | 32.4 ± 1.5*** |
| flunarizine (known compound) | 40 | 10 | 23.7 ± 0.9 |
| | 80 | 9 | 24.6 ± 0.8* |
| nicardipine (known compound) | 80 | 10 | 24.3 ± 1.0 |
| vinpocetine (known compound) | 80 | 10 | 22.5 ± 1.1 |
| Controls | — | 8 | 23.0 ± 1.1 |

*P < 0.05, ***P < 0.001

Example 9

Effect on Bicuculline Convulsion

Wister male rats (age: 7 weeks, weight: 180–220 g) were used for the experiment after they were preliminary bred in the metal cage for 1 week in in a breeding room in which the temperature was controlled at 22±2° C. and the humidity was at 55±10%. They were given pelleted diet (CE-2, product of Nippon Crea) and water ad lib. Prior to submitting the animals to the experiment, they were fasted for 21–23 hours.

Each test compound was dissolved in 0.5% methylcellulose solution and orally administered to each mouse, and 1 hour later 1.75 mg/kg of bicuculline was given intravenously through caudal vein over the period of 15 seconds. Then, the tonic hindpaw extension was observed.

The results are shown in Table 4. The compounds 1c and 2b inhibited the tonic extension dose-dependency. Thus, the compounds have been recognized as possessing the brain protective action.

TABLE 4

| Test Compounds | Quantity Administered (mg/kg oral) | Numbers of Tested Animals | Animals Convulsed/ Animals Tested | Rate of Convulsion Inhibition (%) |
|---|---|---|---|---|
| 1c | 1 | 10 | 8/10 | 20 |
| | 5 | 10 | 5/10 | 50 |
| | 10 | 10 | 1/10 | 90 |
| | 15 | 10 | 0/10 | 100 |
| 2b | 5 | 10 | 6/10 | 40 |
| | 10 | 10 | 5/10 | 50 |
| | 15 | 10 | 2/10 | 80 |
| | 20 | 10 | 0/10 | 100 |
| Controls | 5 | 16 | 14/16 | 13 |

Example 10

Effects on Vertebral Artery Blood Flow and Common Carotid Artery Blood Flow:

Male adult dogs (weight: 10-15 g) were used for the experiment after they were preliminary bred in the metal cage for 1 week in in a breeding room in which the temperature was controlled at 22±2° C. and the humidity was at 55±10%. They were given pelleted diet (CS, product of Oriental Yeast Co.) and water ad lib. Prior to submitting the animals to the experiment, they were fasted for 21-23 hours.

The dogs were anesthetized with sodium pentobarbital and probes for measuring the blood flows were fitted on the right vertebral artery and right common carotid artery. After measuring the control blood flows, the test compounds dissolved in physiological saline were intravenously administered. The vertebral artery blood flow (VBF) and the common carotid artery flow (CCBF) were measured to determine the increments of the blood flow resulting from administration of the test compounds.

The results are shown in Tables 5 and 6. The compounds 1c and 2b increased VBF and CCBF dose-dependently. Thus, these compounds have been recognized as having the cerebral blood flow increasing action.

TABLE 5

| | Increase in VBF and CCBF by the administration of the compound 2b (n = 3) | | | |
|---|---|---|---|---|
| | VBF (Δ%) | | CCBF (Δ%) | |
| Time (min.) | Dosage (mg/kg) | | | |
| | 1 | 3 | 1 | 3 |
| 1 | 7.2 ± 4.9 | 43.1 ± 28.5 | 1.5 ± 1.5 | 7.1 ± 5.6 |
| 2 | 18.6 ± 7.4 | 74.3 ± 23.3 | 5.2 ± 1.6 | 9.8 ± 7.4 |
| 3 | 24.6 ± 8.3 | 78.2 ± 28.2 | 2.4 ± 1.2 | 4.6 ± 4.8 |
| 4 | 17.6 ± 8.8 | 40.5 ± 21.1 | 1.4 ± 1.4 | −1.8 ± 4.3 |
| 5 | 3.7 ± 3.7 | 18.5 ± 12.7 | −1.0 ± 1.0 | −5.9 ± 2.1 |

TABLE 6

| | Increase in VBF and CCBF by the administration of the compound 1c (n = 3) | | | | | |
|---|---|---|---|---|---|---|
| | VBF (Δ%) | | | CCBF (Δ%) | | |
| | Dosage (mg/kg) | | | | | |
| Time (min.) | 0.3 | 1 | 3 | 0.3 | 1 | 3 |
| 1 | 6.3 ± 6.3 | 9.6 ± 5.1 | 44.2 ± 16.3 | 2.4 ± 1.3 | 5.2 ± 0.8 | 9.5 ± 2.7 |
| 2 | 19.7 ± 9.0 | 59.6 ± 33.3 | 154.7 ± 56.5 | 4.5 ± 0.7 | 11.9 ± 4.7 | 19.0 ± 16.1 |
| 3 | 32.2 ± 15.8 | 74.5 ± 36.3 | 173.7 ± 61.6 | 4.5 ± 0.7 | 13.9 ± 7.4 | 14.1 ± 18.0 |
| 4 | 26.5 ± 13.2 | 68.9 ± 39.3 | 143.6 ± 54.0 | 4.5 ± 0.7 | 12.8 ± 7.2 | 12.7 ± 14.2 |
| 5 | 16.1 ± 7.9 | 39.2 ± 27.5 | 111.4 ± 49.6 | 0.8 ± 2.7 | 6.4 ± 3.6 | 9.3 ± 10.8 |
| 10 | 12.5 ± 12.5 | 14.0 ± 8.5 | 65.8 ± 30.5 | 0 ± 0 | 1.1 ± 1.1 | 6.1 ± 5.8 |
| 15 | 15.5 ± 11.3 | 11.7 ± 9.0 | 37.5 ± 18.4 | 2.2 ± 2.8 | 3.6 ± 2.0 | 4.9 ± 5.0 |

Example 11

Measurement of $LD_{50}$ ddY male mice having been preliminary bred in the same manner as Example 7 were orally given the test compounds to determine $LD_{50}$. The results are shown in Table 7.

TABLE 7

| Tested Compounds | 1c | 2b | 3b | 4b | 5b | 6b |
|---|---|---|---|---|---|---|
| $LD_{50}$(mg/kg) | 368 | 450 | 430 | 373 | 510 | 608 |

Example 12

Capsules

Capsules having the following formulation were prepared according to the conventional method.

Ingredients per capsule (150mg)

| | |
|---|---|
| Compound 2b | 20 mg |
| Corn starch | 50 mg |
| Crystallized cellulose | appropriate amount |
| Hydrogenated oil | 3 mg |
| Total | 150 mg |

What is claimed as new and desired to be secured by Letters Patent of the United States is:

1. An indene compound of the formula (I)

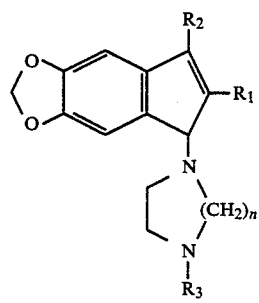

in which $R_1$ represents a lower alkyl group, $R_2$ represents a hydrogen atom, a phenyl group or lower alkyl group, $R_3$ represents a lower alkyl group, and n indicates an integer of 2 or 3; or a salt thereof.

2. A composition for ameliorating cerebral circulation and metabolism, which comprises an effective amount of an indene compound according to claim 1, in combination with a pharmaceutically acceptable carrier or diluent.

* * * * *